United States Patent [19]

Gershon et al.

[11] Patent Number: 5,043,183
[45] Date of Patent: Aug. 27, 1991

[54] ORAL RINSE AND METHOD FOR PLAQUE REMOVAL

[75] Inventors: Sol Gershon, Teaneck; Charles Fox, Fairlawn, both of N.J.; Norton Garfinkle, Boca Raton, Fla.

[73] Assignee: Cambridge Research Laboratories, Inc., New York, N.Y.

[21] Appl. No.: 406,460

[22] Filed: Sep. 13, 1989

[51] Int. Cl.$^5$ .......................... A61K 7/16; A61K 7/18
[52] U.S. Cl. ........................................ 424/52; 424/57
[58] Field of Search ................... 424/495, 257, 52, 57

[56] References Cited

U.S. PATENT DOCUMENTS

| | | | |
|---|---|---|---|
| 1,471,987 | 10/1928 | Vogt | 424/57 |
| 1,691,504 | 11/1928 | Vogt | 424/57 |
| 2,069,157 | 1/1937 | Sahyun | 424/57 |
| 2,955,984 | 10/1960 | Buonocure et al. | 424/57 |
| 3,462,366 | 8/1969 | Luoma | 424/57 |
| 3,671,626 | 6/1972 | Felger | 424/49 |
| 3,927,202 | 12/1975 | Harvey et al. | 424/57 |
| 4,080,440 | 3/1978 | DiGiulio et al. | 424/57 |
| 4,081,526 | 3/1978 | Asakawa et al. | 424/57 |
| 4,097,588 | 6/1978 | Levine | 424/57 |
| 4,097,604 | 6/1978 | Thiele | 424/57 |
| 4,198,394 | 4/1980 | Faunce | |
| 4,203,966 | 5/1980 | Faunce | 424/57 |
| 4,254,101 | 3/1981 | Denny | |
| 4,340,583 | 7/1982 | Wason | 424/57 |
| 4,353,892 | 10/1982 | Caslawsley et al. | 424/57 |
| 4,397,837 | 8/1983 | Raaf et al. | 424/57 |
| 4,405,600 | 9/1983 | Besic | 424/57 |
| 4,460,565 | 7/1984 | Westrate et al. | 424/49 |
| 4,476,107 | 10/1984 | Schmoika | 424/49 |
| 4,532,124 | 7/1985 | Pearce | 424/57 |
| 4,550,018 | 10/1985 | Ambike et al. | 424/52 |
| 4,565,691 | 1/1986 | Jackson | |
| 4,606,912 | 8/1986 | Rudy et al. | 424/52 |
| 4,610,873 | 9/1986 | Rudy et al. | 424/52 |
| 4,657,758 | 4/1987 | Goldemberg | |
| 4,666,708 | 5/1987 | Goldemberg | |

OTHER PUBLICATIONS

Nizel et al., "The Effects of Phosphates on Experimental Dental Caries: A Literature Review", J. Dent. Res., vol. 43, Supplement to No. 6, 1964, pp. 1123-1135.

Englander et al., "Effects of Phosphate Supplements on Cavitation in Hamsters Infected with Caries-Conductive Streptococci", J. Dent. Res., vol. 49, No. 1, Jan.-Feb. 1970, pp. 140-144.

Pruitt et al., "Possible Basis for the Cariostatic Effect of Inorganic Phosphates", Nature, vol. 225, Mar. 28, 1970, p. 1249.

McGaughey et al., "Absorption of Salivary Proteins by Hydroxyapatite: Effects of Phosphate Ions and Interdependence of the Effects of Phosphate and Hydrogen Ions", J. Dent. Res., vol. 53, No. 1, Jan.-Feb. 1974, pp. 121-126.

Drug Products, The Chemical Formulary, vol. 20, 1977, pp. 263-264.

Bailey, "Direct Plaque Removal by a Pre-Brushing Dental Rinse", Clinical Preventive Dentistry, vol. 1, No. 3, May-Jun., 1989, pp. 21-27.

Phosphoric Acid and Phosphates, Encyclopedia of Chemical Technology, 3rd Edition, vol. 17, pp. 441-444.

Turesky et al., "Reduced Plaque Formation by the Chloromethyl Analogue of Vitamin C", Tufts University School of Dental Medicine Report, pp. 41-43.

Primary Examiner—Shep K. Rose

[57] ABSTRACT

This invention relates to improved oral compositions for dental hygiene, and, in particular, to dental rinse and mouthwash formulations containing orthophosphates which upon application to the teeth remove and retard the development of dental plaque on dental surfaces.

15 Claims, No Drawings

ORAL RINSE AND METHOD FOR PLAQUE REMOVAL

BACKGROUND OF THE INVENTION

This application relates to an oral rinse for the disruption of plaque from teeth, and relies upon applicants' discovery that the incorporation of orthophosphates leads to substantial removal of plaque.

Dental plaque is present to a greater or lesser extent on virtually all dental surfaces. Dental plaque is composed of closely matted microorganisms in a matrix made from polysaccharides, proteins and other materials which are, at least in part, of salivary origin. The microorganisms are mainly coccoidal, especially in early plaque, changing in some mouths to filamentous organisms after a few days. Dental plaque presents a significant problem to dental health for several reasons. First, evidence indicates that the microorganisms in dental plaque are a primary factor in dental caries. In addition, the prime etiologic factor in periodontal disease, including gingivitis, is dental plaque.

Moreover, dental plaque is a precursor in calculus formation. Dental calculus (tartar) forms on the surfaces of teeth at the gingival margin and promotes periodontal breakdown by increasing undesirable products in the crevicular pocket area. Supragingival calculus appears principally near orifices of salivary ducts e.g. on lingual surfaces of the lower anterior teeth, on buccal surfaces of the first and second molars, and on the distal surfaces of the posterior molars. In addition to being unsightly from an aesthetic viewpoint, calculus is a constant source of irritation to the gingiva and can make toothbrushing a painful procedure.

Because of these problems associated with plaque, it is important to find means to reduce plaque accumulation on teeth. Regular brushing with a conventional dentifrice for some persons can retard or even prevent the accumulation of significant amounts of dental plaque and calculus. For other persons, however, the plaque film builds up rapidly even with regular brushing, which, in turn, leads to the formation of calculus. Removal by a dentist is the most common method available for individuals to prevent the undesirable consequences of the accumulation of significant amounts of dental calculus. Recently, however, dental rinses have been developed with the stated purpose of loosening plaque on dental surfaces to facilitate its removal during brushing. For example, U.S. Pat. No. 4,657,758, incorporated herein by reference, describes a dental rinse which is an alkaline solution of a surfactant and a detergent builder.

It has now been found that orthophosphates, particularly alkali metal orthophosphates and ammonium orthophosphates, when used in a concentration of about 1.2% to about 10.0% by weight in an oral rinse at pH 5.5–10.5, are highly effective in removing plaque on teeth. While orthophosphates have been used in dental preparations, the ability to act as plaque loosening and removing agents, to applicants' knowledge, has not been recognized. For example, alkali metal phosphate has been shown to be effective in reducing dental caries when added to cariogenic rodent diets. (Nizel et al., J. Dent Res. Supp. to No. 6, 43, 1123 (1964)). A similar result was noted in hamsters, along with the further observation that continuous administration of the phosphate supplement is required to attain this anticaries effectiveness (Englander et al., J. Dent. Res. 49(1), 140 (1970)). This effect has been attributed to a modification of the composition of the protein layer adsorbed on tooth enamel. (Pruitt et al., Nature 225, 1249 (1970)).

Alkali metal phosphates have been used in fluoride dentifrices. U.S. Pat. No. 4,198,394 claims a dentifrice containing sodium dihydrogen phosphate (0.03–0.4%) and stannous fluoride (0.03–0.4%) with a pH of about 2.5 to about 5.5. U.S. Pat. No. 4,565,691 presents an oral hygiene composition which contains alkali metal phosphates in a fluoride-containing dentifrice which utilizes dicalcium phosphate dihydrate, as the abrasive. The phosphates are added to maintain fluoride availability. U.S. Pat. No. 4,254,101 presents dentifrice formulas in which alkali metal phosphates are used as buffers in a fluoride-containing dentifrice. None of these patents are concerned with clear dental rinses or mouthwashes.

Orthophosphates have also been used in certain oral rinses, to protect enamel. For example, an acidulated phosphate fluoride dental rinse from sodium fluoride, acidulated with a mixture of sodium phosphate, monobasic, and phosphoric acid to a level of 0.1M phosphate ion and a pH of 3.0–4.5 is recognized as an over-the-counter anticaries dental rinse drug product [Federal Register, 50 (No. 89):39854–39873, Sept. 30, 1985]. The phosphates are present to protect enamel at the low pH specified.

BRIEF DESCRIPTION OF THE INVENTION

The present invention provides an oral rinse intended for application to dental surfaces for the purpose of removing dental plaque, thereby retarding the accumulation of the plaque on dental surfaces. The oral rinse of this invention comprises an alkali metal orthophosphate or ammonium orthophosphate in an aqueous or aqueous-alcoholic solution with a pH of at least about 5.5 to about 10.5. Preferably, the oral rinse may also include an anionic surfactant in an amount from about 0.05% to about 3.0%, a nonionic surfactant in an amount at least about 0.05% to about 5.0% or both. The alkali metal orthophosphates or ammonium orthophosphates are present in an amount from 1.2% to about 10.0%. It has been found that when an alkali metal phosphate or ammonium phosphate is employed in the dental rinse or mouthwash described above, the ability of the formulation to remove plaque is surprisingly and significantly enhanced. The presence of an anionic or non-ionic surfactant facilitates penetration of the orthophosphates resulting in compositions providing significant removal of plaque from teeth.

In further embodiments of the oral rinse of this invention, effective amounts of various conventional auxiliary materials such as colorants, flavorants, antiseptics, healing agents and the like are advantageously employed in combination with other ingredients.

The oral rinse of this invention may be applied to the surface of the teeth by any conventional process. Preferably, however, the oral rinse is applied by placing a comfortable amount of the oral rinse in the oral cavity and then circulating the rinse about the mouth with the intention of thoroughly soaking the teeth and gums. The substantial removal of oral plaque accomplished through the use of the dental rinse and associated methods of this invention should also serve to reduce the undesirable consequences associated with the buildup of dental plaque particularly gingivitis.

Further advantages and objectives of this invention will be apparent from the detailed description of the invention which follows.

DETAILED DESCRIPTION OF THE INVENTION

It has been discovered that compositions comprising the orthophosphates possess unexpected, significant abilities to remove dental plaque when used as an oral rinse. The term "oral rinse" as used herein encompasses both prebrushing dental rinses and mouthwashes which are generally used after brushing. The various components of such rinses are described below.

Alkali Metal and Ammonium Phosphates

The water-soluble phosphates useful in the current invention include monosodium orthophosphate, disodium orthophosphate, trisodium orthophosphate and the potassium and ammonium orthophosphate equivalents. A detailed description of these salts can be found in Kirk and Othmer, Encyclopedia of Chemical Technology, Third Edition, Volume 17, John Wiley and Sons (1982), pp. 426-472, incorporated herein by reference. The orthophosphate salts can exist in anhydrous or hydrated forms. Either form is acceptable for the desired compositions. The orthophosphate salts are used in the present compositions to provide at least 1.2% to about 10% by weight water soluble orthophosphate or mixtures thereof, preferably from about 1.5% to about 5%.

Anionic Surfactants

Organic surface-active agents are used in the compositions of the present invention to achieve increased prophylactic action and to assist in achieving thorough and complete dispersion of the orthophosphate salts throughout the oral cavity. Suitable examples of anionic surfactants are: water-soluble salts of higher fatty acid monoglyceride monosulfates, such as the sodium salt of the monosulfated monoglyceride of hydrogenated coconut oil fatty acids; higher alkyl sulfates such as sodium lauryl sulfate; alkyl aryl sulfonates; higher alkyl sulfoacetates; and higher fatty acid esters of 1,2 dihydroxypropane sulfonate. Ampholytic surfactants, serving as anions, can also be included in the compositions of the present invention. Examples of such compounds are: sodium or potassium N-lauroyl sarcosine; ethanolamine salts of N-lauroyl, N-myristoyl, or N-palmitoyl sarcosine. Mixtures of anionic surfactants can be employed.

The anionic surfactants are used in the present compositions to provide at least about 0.05% to about 3% anionic compounds and preferably in the range from about 0.1% to about 1%. The preferred anionic surfactant, sodium lauryl sulfate, assists in achieving complete dispersion of the orthophosphate salts throughout the oral cavity and achieves an increase in plaque removal.

Non-Ionic Surfactants

Non-ionic surfactants are used in the compositions of the present invention to achieve prophylactic action, to assist in the dispersion of the orthophosphate salts throughout the oral cavity and to maintain removed plaque in a dispersed state to minimize redeposition on the teeth.

Suitable examples of non-ionic surfactants are the Pluronics ®, polyethylene oxide condensates of alkyl phenols, products derived from the condensation of ethylene oxide with the reaction product of propylene oxide and ethylene diamine, and ethylene oxide condensates of aliphatic alcohols. Also useful are mixtures of laurate esters of sorbitol and sorbitol anhydrides consisting predominantly of the monoester condensed with about 15-25 moles of ethyleneoxide. Tween ® 20 available from I.C.I. Americas, Wilmington, Delaware is particularly useful. Mixtures of non-ionic surfactants can be employed with mixtures of anionic surfactants.

The non-ionic surfactants are used in the present compositions to provide a concentration of at least about 0.05% to about 5% and preferably from about 0.1% to about 1%. The preferred non-ionic, polysorbate 20 (Tween ® 20) assists in achieving dispersion of the orthophosphate salts throughout the oral cavity and maintains plaque in a dispersed state to minimize redeposition on the teeth.

Auxiliary Materials

Effective amounts of various conventional auxiliary materials such as colorants, flavorants, antiseptics, healing agents and the like are advantageously employed in combination with other ingredients. More specifically, formulations of the oral rinse of this invention may include; (1) humectants, e.g. glycerin, sorbitol etc.; (2) sweetening agents, e.g. saccharin, aspartame, cyclamate; (3) flavors, e.g. oil of spearmint, oil of peppermint, menthol, methyl salicylate, oil of cinnamon; (4) coloring agents e.g. FD&C Blue No. 1; (5) detergent builders, e.g. sodium bicarbonate, sodium sulfate, etc.; (6) therapeutic agents, e.g. allantoin, soluble fluorides, urea, fluorophosphates, quaternary salts etc.; and (7) thickening agents, e.g. xanthan gum, sodium carboxymethylcellulose etc.

The oral rinse is prepared by mixing the active ingredients together to form a homogeneous solution of the constituent ingredients. The rinse is used in a conventional manner, that is, by applying a comfortable amount in the mouth, say one tablespoonful, and rinsing it about the dental surfaces. As illustrated by the example below, a striking reduction in the amount of dental plaque on tooth surfaces is accomplished over a relatively brief usage period.

The manner of making and using the present invention will be illustrated further by the following detailed example:

EXAMPLE 1

| Component | Percent by Weight |
| --- | --- |
| Disodium Phosphate (Anhydrous) | 1.350 |
| Monosodium Phosphate (Monohydrate) | 0.150 |
| Sodium Lauryl Sulfate | 0.500 |
| Polysorbate 20 | 0.800 |
| Glycerin | 15.000 |
| Ethyl Alcohol | 6.650 |
| Flavor | 0.075 |
| Saccharin Sodium | 0.020 |
| Distilled Water | 75.455 |
|  | 100.000 |

The glycerin, saccharin sodium, sodium lauryl sulfate, disodium phosphate anhydrous, and monosodium phosphate monohydrate are intimately mixed until the solids are thoroughly wetted with the glycerin. The distilled water is added and the mixture stirred until clear and homogeneous. The flavor, polysorbate 20 and ethyl alcohol are mixed until clear and homogenous.

The flavor mixture is added to the aqueous mixture with stirring during the addition. Stirring is continued until the mixture is clear and homogeneous. The resulting mixture is filtered.

EXAMPLE 2

The following formulations were prepared for clinical evaluation to determine the effectiveness of each formula in removing plaque when 15 ml of product is used for 30 seconds.

| Component | A % | B % |
|---|---|---|
| Disodium phosphate, anhydrous | 1.350 | 0.000 |
| Monosodium phosphate, monohydrate | 0.150 | 0.000 |
| Sodium lauryl sulfate | 0.500 | 0.500 |
| Polysorbate 20 | 0.800 | 0.800 |
| Glycerin | 15.000 | 15.000 |
| Ethyl alcohol | 6.650 | 6.650 |
| Sodium bicarbonate | 0.000 | 0.250 |
| Flavor | 0.075 | 0.075 |
| Saccharin sodium | 0.020 | 0.020 |
| Distilled water | 75.455 | 76.705 |
|  | 100.000 | 100.000 |
| pH | 7.51 | 8.44 |

Formula A is the oral rinse presented in Example 1. Formula B is Formula A without the orthophosphate salts. A small quantity (0.25%) of sodium bicarbonate is used in Formula B to insure stability of the sodium lauryl sulfate. Sodium bicarbonate is not required in Formula A because the orthophosphates provide the desired sodium lauryl sulfate stability.

Subjects were selected from a hospital outpatient dental clinic. All subjects were in good health, were between the ages of 18 and 60, and were able to follow instructions. Excluded were subjects who had oral lesions or systemically related gingival enlargement or who otherwise had oral conditions that interfere with an evaluation of the effects of the rinses. Scoring was done on teeth 3, 9, 12, 19, 25 and 28 (the Ramfjord teeth).

On entry, each subject was scored for plaque on the Ramfjord teeth after application of a plaque disclosing solution. Plaque was scored by the Turesky modification of the Quigley-Hein plaque area index on the buccal and lingual surfaces. The subjects then rinsed for a timed 30 seconds with 15 ml of assigned rinse.

After application of the plaque disclosing solution, a second plaque area assessment was made by the same scorer. The products supplied to the investigator were coded. Neither the investigator nor the subject knew the identity of the test product. Rinse A and rinse B were tested using randomly chosen subjects. Rinse A was evaluated with 105 subjects and rinse B was used by 50 subjects. The results are shown in Table I below.

TABLE I

Clinical Results

| | Rinse A mean ($\bar{x}$) | Rinse B mean ($\bar{x}$) |
|---|---|---|
| Baseline | 2.38 | 2.26 |
| After rinse | 1.73 | 2.14 |
| % Removal | 27.3 | 5.3 |
| p = <.001 for A versus B | | |

The use of rinse B resulted in 5.3% removal of plaque, a small reduction effected by the presence of sodium lauryl sulfate and polysorbate 20. The use of rinse A according to the invention resulted in a 27.3% removal of plaque, a significant increase over rinse B. The improvement is due to the plaque removing effectiveness of the soluble orthophosphate salts. These studies demonstrate clearly that the addition of orthophosphates to the sodium lauryl sulfate and polysorbate 20 rinse results in a significantly greater removal of dental plaque, even in the absence of post rinse brushing.

These data are also directly comparable with data published by L. Bailey, Clinical Preventive Dentistry 11(3):21-27(1989) in which Plax ® a commercially available product in accordance with U.S. Pat. No. 4,657,758 was compared with Listerine ® antiseptic. These results were as follows:

| Sample | % Removal (mean) |
|---|---|
| Control (Placebo) | 2.0 |
| Plax ® (original flavor) | 13.5 |
| Plax ® (soft mint flavor) | 19.2 |
| Listerine ® | 1.3 |

Thus, rinse A according to the invention is superior to the materials tested by Bailey.

EXAMPLE 3

Another formulation was prepared as follows:

| Component | A % |
|---|---|
| Disodium phosphate, anhydrous | 1.350 |
| Monosodium phosphate, monohydrate | 0.150 |
| Urea | 3.000 |
| Sodium lauryl sulfate | 0.500 |
| Polysorbate 20 | 0.800 |
| Glycerin | 15.000 |
| Ethyl alcohol | 6.650 |
| Flavor | 0.075 |
| Saccharin sodium | 0.020 |
| Distilled water | 72.455 |
|  | 100.000 |
| pH | 7.72 |

Clinical testing of this formulation using the method of Example 2 with 104 subjects showed a 21.9% removal of plaque.

The following examples further describe and demonstrate the embodiments within the scope of the present invention:

EXAMPLE 4

| Component | Percent by Weight |
|---|---|
| Disodium phosphate, anhydrous | 9.00 |
| Monosodium phosphate, monohydrate | 0.90 |
| Sodium lauryl sulfate | 0.50 |
| Polysorbate 20 | 0.50 |
| Glycerin | 5.00 |
| Sorbitol (70%) | 14.30 |
| Ethyl alcohol | 6.65 |
| Flavor | 0.05 |
| Saccharin sodium | 0.02 |
| Distilled Water | 63.08 |
| pH = 7.59 | 100.00 |

A similar formulation (Sodium Lauryl Sulfate 0.8%, polysorbate 20 1.5%, pH 7.45) showed some instability due to crystal growth on aging at room temperature.

EXAMPLE 5

| Component | Percent by Weight |
| --- | --- |
| Disodium phosphate, anhydrous | 4.05 |
| Monosodium phosphate, anhydrous | 0.39 |
| Sodium lauryl sulfate | 0.30 |
| Polysorbate 20 | 0.60 |
| Glycerin | 5.00 |
| Sorbitol (70%) | 14.30 |
| Ethyl alcohol | 6.65 |
| Flavor | 0.10 |
| Saccharin sodium | 0.02 |
| Distilled Water | 68.59 |
| pH = 7.53 | 100.00 |

This invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the invention. Accordingly such variations and modifications are considered to be within the purview and scope of the invention and the following claims.

We claim:

1. An oral rinse composition for removing plaque present on dental surfaces consisting essentially of:
   (a) a plaque disrupting component consisting essentially of an alkali metal or ammonium orthophosphate or mixtures thereof in an amount of from 1.2 to 10% by weight and from 0.05 to 8% by weight of one or more surfactants selected from among water-soluble salts of higher fatty acid monoglyceride-monosulfates, higher alkyl sulfates, alkyl aryl sulfonates, higher fatty acid esters of 1,3-dihydroxypropane sulfonate, sodium and potassium N-lauroyl sarcosine, ethanolamine salts of N-lauroyl, N-myristyl and N-palmitoyl sarcosine, polyethylene oxide condensates of alkyl phenols, surfactants derived from the condensation of ethylene oxide with the reaction product of propylene oxide and ethylenediamine and ethylene oxide condensates with aliphatic alcohols and mixtures of esters of sorbitol and sorbitol anhydrides consisting predominantly of the monoester condensed with ethyleneoxide;
   (b) optionally one or more auxiliary materials selected from among humectants, sweetness, flavoring agents, detergent builders, therapeutic agents and thickening agents; and
   (c) an aqueous/alcoholic carrier; wherein the pH of said composition is 5.5 to 10.5.

2. An oral rinse composition according to claim 1, wherein the amount of orthophosphates is from 1.5 to 5%.

3. An oral rinse composition according to claim 2, wherein the alkali metal orthophosphates are selected from the group consisting of mono-, di-, and trisodium and potassium orthophosphates.

4. An oral rinse composition according to claim , wherein the anionic surfactant is sodium lauryl sulfate.

5. An oral rinse composition according to claim , wherein the nonionic surfactant is polyoxyethylene (2)—sorbitan mono laurate.

6. An oral rinse composition according to claim , wherein the amount of nonionic surfactant is from about 0.1% to about 1%.

7. An oral rinse composition according to claim 1 including a water-soluble fluoride compound as a therapeutic agent.

8. An oral rinse composition according to claim 7, wherein the water-soluble fluoride compound is sodium fluoride.

9. An oral rinse composition according to claim 7, wherein the water-soluble fluoride compound is sodium monofluorophosphate.

10. A composition according to claim 1, wherein the plaque disrupting component includes from 0.05 to 3% by weight of an anionic surfactant.

11. A composition according to claim 1, wherein the plaque disrupting component includes from 0.05 to 5% by weight of a nonionic surfactant.

12. A composition according to claim 10, wherein the plaque disrupting component includes from 0.05 to 5% by weight of a nonionic surfactant.

13. A method for disrupting plaque on the surface of teeth comprising applying to the teeth having plaque on the surface an oral rinse comprising an effective plaque removing amount of alkali metal or ammonium orthophosphates or mixtures thereof, wherein the pH of the rinse is from 5.5 to 10.5.

14. A method according to claim 13, wherein the amount of orthophosphate is from 1.2% to 10% by weight.

15. A method according to claim 13, wherein the oral rinse further comprises from 0.05% to 8% of one or more surfactants selected from among anionic and nonionic surfactants.

* * * * *

UNITED STATES PATENT AND TRADEMARK OFFICE
CERTIFICATE OF CORRECTION

PATENT NO. : 5,043,183

DATED : August 27, 1991

INVENTOR(S) : Gershon et al.

It is certified that error appears in the above-identified patent and that said Letters Patent is hereby corrected as shown below:

Col. 7, lines 37-38, "1,3-dihydroxypropane" should read
--1,2-dihydroxypropane--;
Col. 8, line 12, "claim ," should read --claim 10,--;
Col. 8, line 14, "claim ," should read --claim 11,--;
Col. 8, line 16 "(2)" should read --(20)--.
Col. 8, line 17, "claim ," should read --claim 12,--.

Signed and Sealed this

Sixth Day of April, 1993

Attest:

STEPHEN G. KUNIN

*Attesting Officer*  *Acting Commissioner of Patents and Trademarks*